US007141686B2

(12) United States Patent
Dewis et al.

(10) Patent No.: US 7,141,686 B2
(45) Date of Patent: Nov. 28, 2006

(54) E2, E4, Z8-UNDECATRIENOIC ACID AND ESTER AND CARBOXAMIDE DERIVATIVES THEREOF, ORGANOLEPTIC USES THEREOF AND PROCESSES FOR PREPARING SAME

(75) Inventors: Mark L. Dewis, Matawan, NJ (US); Michelle E. Huber, River Vale, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 162 days.

(21) Appl. No.: 10/618,367

(22) Filed: Jul. 10, 2003

(65) Prior Publication Data
US 2005/0010062 A1 Jan. 13, 2005

(51) Int. Cl.
C07C 231/00 (2006.01)
C07C 233/00 (2006.01)
(52) U.S. Cl. .................. 554/69; 554/35; 554/223; 554/224; 554/229; 424/39
(58) Field of Classification Search ................ 554/227, 554/229, 224, 223, 35, 69; 452/34; 424/39
See application file for complete search history.

(56) References Cited

U.S. PATENT DOCUMENTS

| 3,111,127 | A | 11/1963 | Jarboe |
| 4,029,759 | A | 6/1977 | Humbert et al. |
| 4,032,661 | A | 6/1977 | Rowsell et al. |
| 4,150,052 | A | 4/1979 | Watson et al. |
| 4,153,679 | A | 5/1979 | Rowsell et al. |
| 4,185,106 | A | 1/1980 | Dittmar et al. |
| 4,226,988 | A | 10/1980 | Watson et al. |
| 4,296,093 | A | 10/1981 | Rowsell et al. |
| 4,470,982 | A | 9/1984 | Winkler |
| 4,472,421 | A | 9/1984 | Buchel et al. |
| 5,009,893 | A | 4/1991 | Cherukuri et al. |
| 5,545,424 | A | 8/1996 | Nakatsu et al. |
| 5,624,666 | A | 4/1997 | Coffindaffer et al. |
| 5,641,480 | A | 6/1997 | Vermeer |
| 5,725,865 | A | 3/1998 | Mane et al. |
| 5,730,965 | A | 3/1998 | Rapaport |
| 5,843,466 | A | 12/1998 | Mane et al. |
| 5,955,066 | A | 9/1999 | Sako et al. |
| 6,096,324 | A | 8/2000 | Mansouri |
| 6,110,520 | A | 8/2000 | He et al. |
| 6,200,554 | B1 | 3/2001 | Yeoh et al. |
| 6,210,695 | B1 | 4/2001 | Beerse et al. |
| 6,248,315 | B1 | 6/2001 | Young et al. |
| 6,251,463 | B1 | 6/2001 | Rossy et al. |
| 6,294,186 | B1 | 9/2001 | Beerse et al. |
| 6,297,203 | B1 | 10/2001 | Guskey et al. |
| 6,299,900 | B1 | 10/2001 | Reed et al. |
| 6,303,817 | B1 | 10/2001 | Boden et al. |
| PP12,213 | P2 | 11/2001 | Zimmermann |
| 6,328,982 | B1 | 12/2001 | Shiroyama et al. |
| 6,333,180 | B1 | 12/2001 | Farbood et al. |
| 6,338,855 | B1 | 1/2002 | Albacarys et al. |
| 6,365,215 | B1 | 4/2002 | Grainger et al. |
| 6,365,601 | B1 | 4/2002 | Gaikar et al. |
| 6,391,886 | B1 | 5/2002 | Lee |
| 6,451,844 | B1 | 9/2002 | Watkins et al. |
| 6,455,080 | B1 | 9/2002 | Wolf et al. |
| 6,544,499 | B1 | 4/2003 | Glenn, Jr. et al. |
| 6,572,914 | B1 | 6/2003 | Borlinghaus |
| 6,576,224 | B1 | 6/2003 | Osbakken et al. |
| 6,576,225 | B1 | 6/2003 | Kilcher et al. |
| 6,576,228 | B1 | 6/2003 | Crookham et al. |
| 6,579,513 | B1 | 6/2003 | Tashjian et al. |
| 6,579,514 | B1 | 6/2003 | Hall et al. |
| 6,579,516 | B1 | 6/2003 | Mansouri |

(Continued)

FOREIGN PATENT DOCUMENTS

EP 1 121 927 A2 2/2001

(Continued)

OTHER PUBLICATIONS

Galophin et al., Abs. pf Papers, 224th ACS National Meeting, Boston, MA, Aug. 18022, 2002, pp. 139-152.*

(Continued)

Primary Examiner—Deborah D. Carr
(74) Attorney, Agent, or Firm—Elizabeth M. Quirk

(57) ABSTRACT

Described is a genus of E2,E4,Z8-undecatrienoic acid derivatives defined according to the structure:

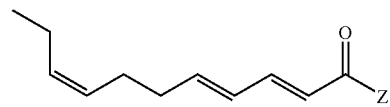

wherein Z represents —OR" or —NRR' with the provisos that when Z is —OR", R" is hydrogen, $C_1$–$C_6$ straight chain or branched-chain alkyl or $C_3$–$C_6$ straight chain or branched-chain alkenyl; and when Z is —NRR', R represents, in the alternative, hydrogen, methyl or ethyl and R' represents methyl, ethyl, n-propyl, cyclopropyl, isopropyl, n-butyl, sec-butyl, isobutyl, 2-methylbutyl, cyclobutyl,

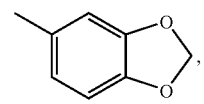

cyclopentyl or allyl. The E2,E4,Z8-undecatrienoic acid derivatives are useful in imparting, augmenting and/or enhancing flavors, aromas and somatosensory effects in or to consumable materials such as foods, beverages, skin care products, oral care products, medicinal products and the like. Also described is a synthesis process for producing such derivatives.

4 Claims, No Drawings

U.S. PATENT DOCUMENTS

| | | | |
|---|---|---|---|
| 6,579,535 | B1 | 6/2003 | Valentine et al. |
| 6,579,543 | B1 | 6/2003 | McClung |
| 2001/0032645 | A1 | 10/2001 | Cronk et al. |
| 2001/0043912 | A1 | 11/2001 | Michael |
| 2002/0012640 | A1 | 1/2002 | Mohammadi et al. |
| 2002/0039591 | A1 | 4/2002 | Dahle |
| 2002/0122778 | A1 | 9/2002 | Wolfson |
| 2002/0142015 | A1 | 10/2002 | Kumamoto et al. |
| 2002/0173436 | A1 | 11/2002 | Sonnenberg et al. |
| 2003/0035784 | A1 | 2/2003 | Inoue et al. |
| 2003/0068330 | A1 | 4/2003 | Goto et al. |
| 2003/0072842 | A1 | 4/2003 | Johnson et al. |
| 2003/0082124 | A1 | 5/2003 | Hammer |
| 2003/0082129 | A1 | 5/2003 | Buckingham et al. |
| 2003/0082271 | A1 | 5/2003 | Wolf et al. |
| 2003/0095936 | A1 | 5/2003 | Light |
| 2003/0095938 | A1 | 5/2003 | Casero |
| 2003/0113357 | A1 | 6/2003 | Bell et al. |
| 2003/0152682 | A1 | 8/2003 | Ley et al. |
| 2004/0241312 | A1 | 12/2004 | Gatfield et al. |

FOREIGN PATENT DOCUMENTS

| | | |
|---|---|---|
| EP | 1 121 927 A2 | 8/2001 |
| EP | 1 122 233 A1 | 8/2001 |
| JP | 56087505 | 7/1981 |
| WO | WO 93/23005 | 11/1993 |
| WO | WO 98/07404 | 2/1998 |
| WO | WO 99/07235 | 2/1999 |
| WO | WO 00/45815 | 8/2000 |
| WO | WO 02/051392 | 4/2002 |
| WO | WO 2004/000787 A2 | 12/2003 |
| WO | WO 2004/011415 | 2/2004 |

OTHER PUBLICATIONS

ACS Symposium Series 867, Challenges in Taste Chemistry and Biology, Sponsored by the ACS Division of Agricultural and Food Chemistry, Chapter 9, Pungent and Tingling Compounds in Asian Cuisine, Galopin, et al. pp. 139-152.

U.S. Appl. No. 611,025, filed Jul. 1, 2003, Dewis et al.

Search for Unsaturated Dienoic Acid Compounds GRAS Flavoring Substances 20, Food Technology, vol. 55, No. 12, Dec. 2001 at p. 53.

Rule, et al. Optical Activity and the Polarity of Substituent Groups Part VIII. Growing-chain Effects and the Ortho-Effect in Benzoic Esters, J.Chem.Soc 1928 (Part I), pp. 1347-1361.

SciFinder (Nov. 20, 2002; Trademark of Chemical Abstracts Service), to wit: malonamic acid, p-menth-3-yl ester, ±-(8C1) having CAS Registry No. 6129-88-0.

Jaloner, et al. A Molecular Approach to Flavor Synthesis. I. Menthol Esters of Varying Size and Polarity, Journal of Polymer Science:Polymer Chemistry Edition, vol. 18, 2933-2940 (1980).

Ottinger, et al, Systematic Studies on Structure and Physiological Activity of Cyclic Alpha-Keto Enamines, a Novel Class of "Cooling" Compounds, J.Agric.Food Chem., 2001,49,5383-5390.

Nakatani, et al, Pungent Alkamides from *Spilanthes acmella* L. var. oleracea Clarke, Biosci. Biotech. Biochem., 56(5), 759-762 (1992).

Gamboa-Leon, et al., Isbutylamide numbing agents of toothache grass, Biochemical Systematics and Ecology 28 (2000), 1019-1021.

Rameswak, et al, Bioactive N-isobutylamides from flower buds of *Spilanthes acmella*, Phytochemistry 51, (1999), 729-732.

Snider, et al, Synthesis of the N- (1E)-Alkenyl) -2z, 4z) -heptadienamide Side Chain of Salicylihalamide A and Apicularens A and B, Organic Letters (2000), vol. 2, No. 3, pp. 407-408.

Crombie, Amides of Vegetable origin, Part VII, Synthesis of N-isobutyldodeca-trans-2:trans-4:trans-8- and trans-2:trans-4:cis-8-trienamide and their relation to Sanshool I, J.Chem.Soc., 1955, pp. 4244-4249.

Furber, et al, Stereospecific Diene Synthesis using Acetylene Carbocupration; Preparation of Navel Orangeworm Pheremone and Leukotriene Analogues, J.Chem.Soc. Perkin Trans.I, 1986, pp. 1809-1815.

Tanaka, et al, Structure and Synthesis of a New Hypotensive Vasodilator Isolated from Streptomyces Aureofaciens, Tetrahedron Letters, vol. 22, No. 35, pp. 3421-3422, 1981.

U.S. Appl. No. 10/411,672, filed Apr. 11, 2003, Dewis et al.

U.S. Appl. No. 10/643,542, filed Aug. 19, 2003, Flammer et al.

Prior Art Submission Under 37 CFR 1.291.

English abstract of Saureamide In Hochruckextrakten Aus Muntokpfeffer in English. H. Kollmannsberger und S. Nitz, Chem. Mikrobiol. Technol. Lebensm. 14, 87-94 (1992).

"Pellitorine Isomers. II. The Synthesis of N-Isobutyl-trans-2, trans-4-decadienamide[1,2,3]", Martine Jacobson, vol. 75, Jun. 5, 1953, pp. 2584-2586.

"Alkamides from *Artemisia dracunculus*", Bouchra Saadali et al., Phytochemistry, Pergamon Press, Vol. 58, No. 7, Dec. 2001, pp. 1083-1086.

"Isobutylamide numbing agents of toothache grass, *Ctenium aromaticum*" Rubi Gamboa-Leon et al., Biochemical Systematics and ecology, vol. 28, 2000, pp. 1019-1021.

ACS Symposium Series 867, Challenges in Taste Chemistry and Biology, Sponsored by the ACS Division of Agricultural and Food Chemistry, Chapter 9, Pungent and Tingling Compounds in Asian Cuisine, Galopin, et al, pp. 139-152, 2004.

* cited by examiner

E2, E4, Z8-UNDECATRIENOIC ACID AND ESTER AND CARBOXAMIDE DERIVATIVES THEREOF, ORGANOLEPTIC USES THEREOF AND PROCESSES FOR PREPARING SAME

FIELD OF THE INVENTION

E2,E4,Z8-Undecatrienoic acid and ester and amide derivatives thereof having beneficial flavor and sensory attributes in the oral cavity and on skin.

BACKGROUND OF THE INVENTION

The prior art discloses the presence of $C_{10}$, $C_{11}$ and $C_{12}$ alkatrienoic acids and ester and amide derivatives thereof in a wide variety of botanicals the use thereof to impart flavor and/or a tingling and/or warming sensations in the oral cavity and on skin when used in foodstuffs, chewing gum, oral care products, hair care products, colognes, topical cosmetic products or medicinal products. Such $C_{10}$, $C_{11}$ and $C_{12}$ alkatrienoic acids and ester and amide derivatives thereof are also disclosed as exhibiting biological activity, most notably anti-bacterial, anti-fungal and insecticidal activity. The most significant compounds which are members of the genus: "$C_{10}$, $C_{11}$ and $C_{12}$ alkatrienoic acids and ester and amide derivatives thereof" are those disclosed as follows:

(a) Amides:

Spilanthol or Affinin having the structure

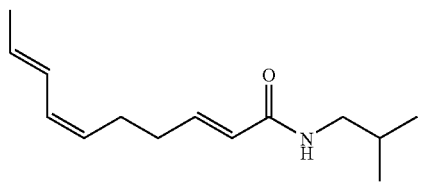

the use of which in oral care, skin care and medicinal products is disclosed in Nakanatsu et al, Published European Patent Application EP 1,121,927 A2; the use of which as an oral sensate, flavor enhancer and potentiator is disclosed in U.S. Published patent application 2002/0122778 A1; and the pungency of which is disclosed in Nakatani et al "Pungent Alkamides from *Spilanthes acmella* L. var. *oleracea* Clarke, *Biosci. Biotech. Biochem.*, 56(5), 759–762 (1992);

Isoaffinin having the structure:

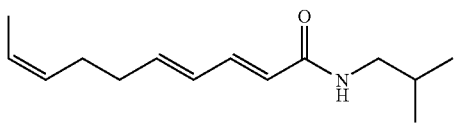

disclosed in Gamboa-Leon et al., "Isobutylamide numbing agents of toothache grass", *Biochemical Systematics and Ecology* 28 (2000)1019–1021;

N-isobutyl E2, Z7, E9-undecatrienamide having the structure:

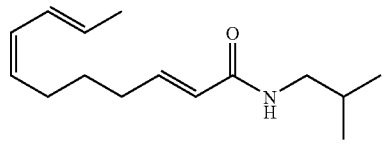

disclosed in Rameswak et al., "Bioactive N-isobutylamides from flower buds of *Spilanthes acmella*", *Phytochemistry* 51 (1999) 729–732;

The disclosure of the compound having the structure:

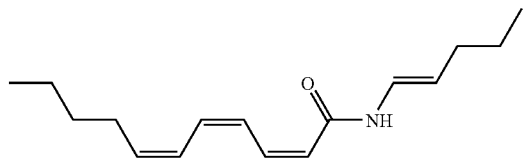

by Snider et al., "Synthesis of the N-((1E)-Alkenyl)-(2Z, 4Z)-heptadienamide Side Clain of Salicilihalamide A and Apicularens A and B", *Organic Letters* (2000), Vol.2, No. 3, pp. 407–408.

(b) Acids:

The presence of dodecatrienoic acid (structure not specified) in a Hop Plant named "YCR Accession No. 14" having an aroma with sharp, floral and spicy notes, as disclosed in Zimmermann, U.S. Plant Patent PP12,213 P2;

The disclosure of the compound having the structure:

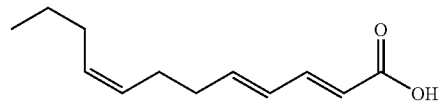

by Crombie, "*Amides of Vegetable Origin, Part VII, Synthesis of* N-isobutyldodeca-trans-2:trans-4:trans-8- and trans-2:trans-4:cis-8-trienamide *and their relation to Sanshool I*", J.Chem.Soc. 1955, pp. 4244–4249.

Published application for U.S. Patent 2003/0068330 A1 published on Apr. 10, 2003 discloses 2,6,10-dodecatrienoic acid (without specifying any particular isomer thereof) for potentiating the activity of Nerve Growth Factor (NGF).

(c) Esters:

The disclosure of the compound having the structure:

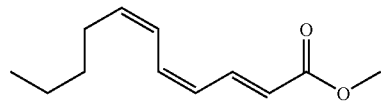

by Furber et al., "Stereospecific Diene Synthesis using Acetylene Carbocupration; Preparation of Navel Orangeworm Pheremone and Leukotriene Analogues", *J. Chem. Soc. Perkin Trans. I*, 1986, pp. 1809–1815;

The disclosure of the compound having the structure:

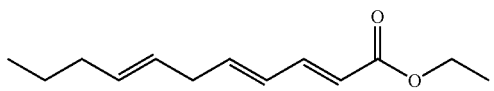

by Tanaka et al., "Structure and Synthesis of a New Hypotensive Vasodilator Isolated from *Streptomyces Aureofaciens*", *Tetrahedron Letters*, Vol. 22, No. 35, pp. 3421–3422, 1981.

Despite the existence in the prior art and in commerce of such a vast number of $C_{10}$, $C_{11}$, and $C_{12}$ alkatrienoic acids and ester and amide derivatives thereof, there is an increasing ongoing need for flavor ingredients, skin care ingredients, oral care ingredients and hair care ingredients that exhibit organoleptically-acceptable somatosensory activity or flavor property, particularly at relatively low threshold levels.

SUMMARY OF THE INVENTION

Our invention relates to novel compounds which are members of the genus:"E2,E4,Z8-undecatrienoic acid and ester and amide derivatives thereof" and a process for augmenting, enhancing or imparting an aroma or taste or somatosensory effect in or to a consumable material which is, in the alternative, a foodstuff, a beverage, a chewing gum, an oral care product, a nasal care product, a cologne, a skin care product, a hair care product, a topical cosmetic product or a medicinal product comprising the step of adding to said consumable material a taste or aroma or somatosensory effect-augmenting, enhancing or imparting quantity and concentration of at least one E2,E4,Z8-undecatrienoic acid derivative defined according to the structure:

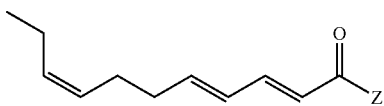

wherein Z represents —OR" or —NRR' with the provisos that when Z is —OR", R" is hydrogen, $C_1$–$C_6$ straight chain or branched-chain alkyl or $C_3$–$C_6$ straight chain or branched-chain alkenyl; and when Z is —NRR', R represents, in the alternative, hydrogen, methyl or ethyl and R' represents methyl, ethyl, n-propyl, cyclopropyl, isopropyl, n-butyl, sec-butyl, isobutyl, 2-methylbutyl, cyclobutyl,

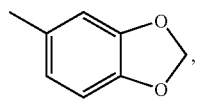

cyclopentyl or allyl.

More specifically, and more preferably, our invention is directed to augmenting or imparting a flavor or somatosensory effect to a foodstuff, chewing gum, medicinal product, toothpaste, alcoholic beverage, aqueous beverage, dairy product, confection, chocolate, sweet composition or savory composition comprising the step of adding to foodstuff, chewing gum, medicinal product, toothpaste, alcoholic beverage, aqueous beverage, dairy product, confection, chocolate, sweet composition or savory composition a flavor or sensation augmenting, enhancing or imparting quantity and concentration of at least one E2,E4,Z8-undecatrienoic acid derivative defined according to the structure:

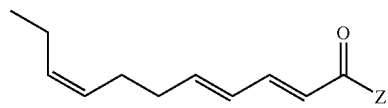

wherein the moiety Z is defined supra.

As used herein the compounds of our invention having the structure:

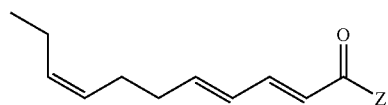

will be referred hereinafter to as "2,4,8-undecatrienoic acid derivatives".

Our invention is also directed to a synthesis process for preparing the 2,4,8-undecatrienoic acid derivatives of our invention by means of first oxidizing the E2, E4, Z8-undecatrienal with silver(I)oxide in aqueous alkali metal hydroxide media followed by acidifcation in order to form the E2, E4, Z8-undecatrienoic acid, which may be utilized as such for its organoleptic and/or somatosensory properties in consumable materials; or which may be further reacted with an alkyl haloformate in admixture with a tertiary amine base in order to form an intermediate which, in turn is reacted with either (a) an amine having the formula RR'NH in order to form a member of the E2, E4, Z8-undecatrienoic acid amide subgenus of our invention or (b) an alcohol having the formula R"OH in order to form a member of the E2, E4, Z8-undecatrienoic acid ester subgenus of our invention.

DETAILED DESCRIPTION OF THE INVENTION

Our invention specifically relates to the novel compositions which are 2,4,8-undecatrienoic acid derivatives which are members of the genus having the structure:

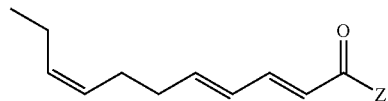

wherein the moiety Z is defined supra, and uses thereof preferably in augmenting or imparting an olfactory effect, flavor or a sensation such as a taste or somatosensory effect to a foodstuff, chewing gum, medicinal product, toothpaste, alcoholic beverage, aqueous beverage, dairy product, confection, chocolate, sweet composition or savory composition particularly providing (a) flavor (b) tingle sensation (c) warming/burning sensation (d) numbing sensation (e) umami taste and (f) salt effects.

Specific members of the 2,4,8-undecatrienoic acid derivative genus of our invention have organoleptic and somatosensory properties as set forth in the following Table I:

TABLE I

| Z | R | R' | R" | Compound | Primary Flavor or Sensory Characteristic |
|---|---|---|---|---|---|
| —NRR' | H | isobutyl | N/A | N-isobutyl E2,E4,Z8-undecatrienamide | Strong tingle at 10 ppm. Green, cucumber and melon flavor with pleasant seashore aroma. |
| —NRR' | methyl | methyl | N/A | N,N-dimethyl E2,E4,Z8-undecatrienamide | At 1 ppm, a flaxseed oil, cod liver oil taste with light tingle and pleasant seashore aroma nuances. |
| —OR" | N/A | N/A | H | E2,E4,Z8-undecatrienoic acid | At 1 ppm in water, a cod liver oil taste with green, fatty nuances. |
| —OR" | N/A | N/A | —CH$_3$ | Methyl E2,E4,Z8-undecatrienoate | At 1 ppm, a pleasant seashore aroma, and a sardine-like taste having a fruity topnote and an aesthetically pleasing astringent effect. |

The following Table II sets forth examples of processes and compositions where the 2,4,8-undecatrienoic acid derivatives of our invention are utilized. Each of the useful ingredients set forth in the cited references, including the examples thereof is usable in the practice of our invention:

TABLE II

| Nature of Use of the 2,4,8-Undecatrienoic Acid Derivatives of our Invention | Reference Containing Examples Where the 2,4,8-Undecatrienoic Acid Derivative of our Invention are Utilizable |
|---|---|
| Skin care | U.S. Pat. No. 6,096,324 |
| Cosmetics, toiletries and bath agents | U.S. Pat. No. 6,328,982 |
| Skin care, cosmetic and hair care compositions | U.S. Pat. No. 6,544,499 |
| Nasal cavity care compositions | U.S. Pat. No. 6,576,224 |
| Dental care compositions | U.S. Pat. No. 6,576,225 |
| Personal wash sunscreen compositions | U.S. Pat. No. 6,576,228 |
| Hair Care Compositions | Application for U.S. Patent 2001/0043912 A1 published on Nov. 22, 2001 |
| Skin care compositions | Application for U.S. Patent 2002/0039591 A1 published on Apr. 4, 2002 |
| Oral sensates, flavor enhancers and potentiators | Application for U.S. Patent 2002/0122778 A1 published on Sep. 5, 2002 |
| Hair care compositions | Application for U.S. Patent 2003/0035784 A1 published on Feb. 20, 2003 |
| Hair and scalp care compositions | Application for U.S. Patent 2003/0095938 A1 published on May 22, 2003 |
| Food, pharmaceutical and personal care products | European Published Application EP 1,121,927 A2 published Aug. 8, 2001 |
| Anti-dandruff and anti-itch compositions | Application for U.S. Patent 10/067,596 filed on Feb. 5, 2002 (IFF-25) |
| Taste and sensory effect compositions | Application for U.S. Patent 10/411,672 filed on Apr. 11, 2003 (IFF-53) |

As used herein olfactory effective amount is understood to mean the amount of compound in flavor compositions, oral care compositions, nasal care compositions, skin care compositions, hair and scalp care compositions, cosmetic compositions and other consumable materials as defined supra, the individual component will contribute to its particular olfactory characteristics, but the flavor, taste and aroma effect on the overall composition will be the sum of the effects of each of the flavor ingredients. As used herein taste effects include salt and umami effects. Thus the compounds of the invention can be used to alter the taste characteristics of the flavor composition by modifying the taste reaction contributed by another ingredient in the composition. The amount will vary depending on many factors including other ingredients, their relative amounts and the effect that is desired.

The level of 2,4,8-undecatrienoic acid derivatives used in products is greater than 10 parts per billion, generally provided at a level of from about 50 parts per billion to about 200 parts per million in the finished product, more preferably from about 100 parts per billion to about 100 parts per million by weight.

The usage level of 2,4,8-undecatrienoic acid derivatives varies depending on the product in which the 2,4,8-undecatrienoic acid derivatives are employed. For example, alcoholic beverages the usage level is from about 0.5 to about 25 parts per million, preferably from about 2 to about 10 and most preferably from about 5 to about 10 parts per million by weight. Non-alcoholic beverages are flavored at levels of from about 25 parts per billion to about 2 parts per million, preferably from about 100 parts per billion to about 0.5 parts per million and in highly preferred situations of from about 150 to about 400 parts per billion. Snack foods can be advantageously flavored using 2,4,8-undecatrienoic acid derivatives of the present invention at levels of from about 5 to about 250 parts per million, preferably from about 25 to about 200 and most preferably from about 35 to about 75 parts per million by weight.

The term "foodstuff" as used herein includes both solid and liquid ingestible materials for man or animals, which materials usually do, but need not, have nutritional value. Thus, foodstuffs include meats, gravies, soups, convenience foods, malt, alcoholic and other beverages, milk and dairy products, seafood, including fish, crustaceans, mollusks and the like, candies, vegetables, cereals, soft drinks, snacks, dog and cat foods, other veterinary products and the like.

When the 2,4,8-undecatrienoic acid derivative compounds of this invention are used in a flavoring composition, they can be combined with conventional flavoring materials or adjuvants. Such co-ingredients or flavor adjuvants are well known in the art for such use and have been extensively described in the literature. Requirements of such adjuvant materials are: (1) that they be non-reactive with the 2,4,8-undecatrienoic acid derivatives of our invention; (2) that they be organoleptically compatible with the 2,4,8-undecatrienoic acid derivatives of our invention whereby the flavor of the ultimate consumable material to which the 2,4,8-undecatrienoic acid derivatives are added is not detrimentally affected by the use of the adjuvant; and (3) that they be ingestible acceptable and thus nontoxic or otherwise non-deleterious. Apart from these requirements, conventional materials can be used and broadly include other flavor materials, vehicles, stabilizers, thickeners, surface active agents, conditioners and flavor intensifiers.

Such conventional flavoring materials include saturated fatty acids, unsaturated fatty acids and amino acids; alcohols including primary and secondary alcohols, esters, carbonyl compounds including ketones, other than the 2,4,8-undecatrienoic acid derivatives of our invention and aldehydes; lactones; other cyclic organic materials including benzene derivatives, acyclic compounds, heterocyclics such as furans, pyridines, pyrazines and the like; sulfur-containing compounds including thiols, sulfides, disulfides and the like; proteins; lipids, carbohydrates; so-called flavor potentiators such as monosodium glutamate; magnesium glutamate, calcium glutamate, guanylates and inosinates; natural flavoring materials such as hydrolyzates, cocoa, vanilla and caramel; essential oils and extracts such as anise oil, clove oil and the like and artificial flavoring materials such as vanillyl butyl ether, ethyl vanillin and the like.

Specific preferred flavor adjuvants include but are not limited to the following: anise oil; ethyl-2-methyl butyrate; vanillin; cis-3-heptenol; cis-3-hexenol; trans-2-heptenal; butyl valerate; 2,3-diethyl pyrazine; methyl cyclo-pentenolone; benzaldehyde; valerian oil; 3,4-dimeth-oxyphenol; amyl acetate; amyl cinnamate; γ-butyryl lactone; furfural; trimethyl pyrazine; phenyl acetic acid; isovaleraldehyde; ethyl maltol; ethyl vanillin; ethyl valerate; ethyl butyrate; cocoa extract; coffee extract; peppermint oil; spearmint oil; clove oil; anethol; cardamom oil; wintergreen oil; cinnamic aldehyde; ethyl-2-methyl valerate; γ-hexenyl lactone; 2,4-decadienal; 2,4-heptadienal; methyl thiazole alcohol (4-methyl-5-β-hydroxyethyl thiazole); 2-methyl butanethiol; 4-mercapto-2-butanone; 3-mercapto-2-pentanone; 1-mercapto-2-propane; benzaldehyde; furfural; furfuryl alcohol; 2-mercapto propionic acid; alkyl pyrazine; methyl pyrazine; 2-ethyl-3-methyl pyrazine; tetramethyl pyrazine; polysulfides; dipropyl disulfide; methyl benzyl disulfide; alkyl thiophene; 2,3-dimethyl thiophene; 5-methyl furfural; acetyl furan; 2,4-decadienal; guaiacol; phenyl acetaldehyde; β-decalactone; d-limonene; acetoin; amyl acetate; maltol; ethyl butyrate; levulinic acid; piperonal; ethyl acetate; n-octanal; n-pentanal; n-hexanal; diacetyl; monosodium glutamate; monopotassium glutamate; sulfur-containing amino acids, e.g., cysteine; hydrolyzed vegetable protein; 2-methylfuran-3-thiol; 2-methyldihydrofuran-3-thiol; 2,5-dimethylfuran-3-thiol; hydrolyzed fish protein; tetramethyl pyrazine; propylpropenyl disulfide; propylpropenyl trisulfide; diallyl disulfide; diallyl trisulfide; dipropenyl disulfide; dipropenyl trisulfide; 4-methyl-2-[(methylthio)-ethyl]-1,3-dithiolane; 4,5-dimethyl-2-(methylthiomethyl)-1,3-dithiolne; and 4-methyl-2-(methylthiomethyl)-1,3-dithiolane. These and other flavor ingredients are provided in U.S. Pat. Nos. 6,110,520 and 6,333,180.

The 2,4,8-undecatrienoic acid derivatives of our invention or compositions incorporating them, as mentioned above, can be combined with one or more vehicles or carriers for adding them to the particular product. Vehicles can be water-soluble or oil-soluble edible or otherwise suitable materials such as triacetin, vegetable oil, triethyl citrate, ethyl alcohol, propylene glycol, water and the like. Carriers include materials such as gum arabic, carrageenan, xanthan gum, guar gum and the like.

2,4,8-undecatrienoic acid derivatives prepared according to our invention can be incorporated with the carriers by conventional means such as spray-drying, extrusion, drum-drying and the like. Such carriers can also include materials for coacervating the 2,4,8-undecatrienoic acid derivatives of our invention to provide encapsulated products, as set forth supra. When the carrier is an emulsion, the flavoring composition can also contain emulsifiers such as mono- and diglycerides or fatty acids and the like. With these carriers or vehicles, the desired physical form of the compositions can be prepared.

The quantity of 2,4,8-undecatrienoic acid derivatives utilized should be sufficient to impart the desired flavor characteristic to the product, but on the other hand, the use of an excessive amount of 2,4,8-undecatrienoic acid derivatives is not only wasteful and uneconomical, but in some instances, too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage, if any, to which the product will be subjected; and the preconsumption treatment such as baking, frying and so on, given to the product by the ultimate consumer. Accordingly, the terminology "effective amount" and "sufficient amount" is understood in the context of the present invention to be quantitatively adequate to alter the flavor of the foodstuff.

With reference to the novel compounds of our invention, the synthesis is effected by means of the oxidation of E2,E4,Z8-undecatrienal with silver (I) oxide in sodium hydroxide solution. Acidification liberates the E2,E4,Z8-undecatrienoic acid. Subsequent reaction with ethyl chloroformate in the presence of triethylamine and further reaction of the intermediate with amine or alcohol (added either directly or in solution) according to the scheme:

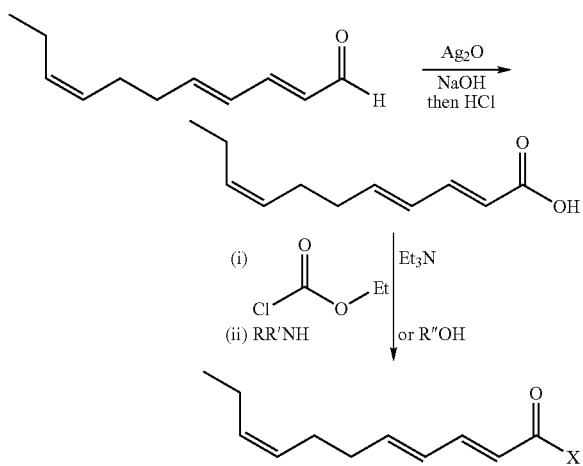

wherein X represents —OR" or —NRR' as set forth in the examples herein and wherein when X is —OR", R" is $C_1$–$C_6$ straight chain or branched-chain alkyl or $C_3$–$C_6$ straight chain or branched-chain alkenyl; and when X is —NRR', R represents, in the alternative, hydrogen, methyl or ethyl and R' represents methyl, ethyl, n-propyl, cyclopropyl, isopropyl, n-butyl, sec-butyl, isobutyl, 2-methylbutyl, cyclobutyl,

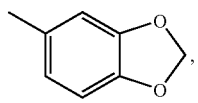

cyclopentyl or allyl. The 2,4,8-undecatrienal is added to a suspension of silver (I) oxide (1.1 eq) in water. The mixture is stirred at 20° C. and 50% sodium hydroxide solution (equal weight to the aldehyde), is added over 30 minutes allowing the batch to exotherm to 60° C. The solution is filtered through celite, and the aqueous filtrate acidified to pH 1 with hydrochloric acid solution, to give 2,4,8-undecatrienoic acid.

The 2,4,8-undecatrienoic acid may be isolated and utilized for its organoleptic properties, or it may be dissolved in an solvent such as n-hexane, toluene, chloroform, tetrahydrofuran (THF) or dichloromethane to which an alkyl haloformate, preferably ethylchloroformate is added in 1.0 to 2.0 equivalents at temperature ranging from 0° C. to room temperature, most preferably from 10° C. to 20° C. The resulting solution is cooled to −10° C. to −30° C., and an aromatic or aliphatic tertiary amine such as pyridine, 4(N, N-dimethylamino)pyridine or triethylamine is added in 1.0 to 2.0 equivalents such that the temperature range is below 0° C. and the mixture aged for 1 hour. The mixture is filtered, and the filtrate cooled to 0° C. At this point an intermediate having, for example the structure:

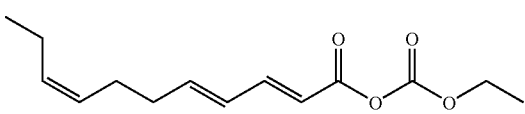

is formed, when the alkyl haloformate is ethyl chloroformate.

For Amides:

The amine is added in 1.0 to 7.0 equivalents either neat or as a solution in THF and the reaction is aged for about 1–3 hours at room temperature. The reaction is quenched with 10% aqueous hydrochloric acid, washed with 10% sodium hydroxide followed by sodium chloride solution, and the solvent removed.

The crude product is purified by distillation or recrystallization depending on the physical properties. The reaction occurs in 40–80% mole yield based on 2,4,8-undecatrienoic acid.

For Esters:

An alcohol of the formula R"OH, e.g., ethyl alcohol (10 eq) is added and the reaction is stirred overnight at room temperature. The reaction is quenched with 10% aqueous hydrochloric acid, washed 5% sodium hydroxide solution and finally with water and the solvent is removed.

The crude product is purified by distillation and the reaction occurs in 60–85% mole yield based on 2,4,8-undecatrienoic acid.

The 2,4,8-undecatrienoic acid derivatives of the present invention can be admixed with other flavoring agents and incorporated into foodstuffs and other products using techniques well known to those with ordinary skill in the art. Most commonly the 2,4,8-undecatrienoic acid derivatives are simply admixed using the desired ingredients within the proportions stated.

The following examples are provided as specific embodiments of the present invention. Other modifications of this invention will be readily apparent to those skilled in the art, without departing from the scope of this invention. As used herein, both the specification and the following examples all percentages are weight percent unless noted to the contrary.

EXAMPLE 1

Preparation of Materials of the Present Invention

The following reaction sequence was used to prepare the specific compounds described by the NMR data set forth below:

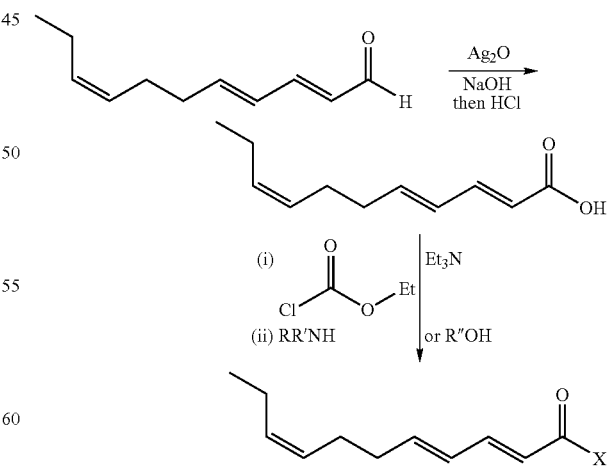

2,4,8-Undecatrienal is added to a suspension of silver (I) oxide (1.1 eq) in water. The mixture is stirred at 20° C. and concentrated sodium hydroxide solution (equal weight to the aldehyde), is added over 30 minutes allowing the batch to exotherm to 60° C. The solution is filtered through celite, and the aqueous filtrate acidified to pH 1 with hydrochloric acid solution, to give 2,4,8-undecatrienoic acid.

2,4,8-undecatrienoic acid is dissolved in dichloromethane to which ethylchloroformate is added in 1.0 to 2.0 equivalents at temperature ranging from 0° C. to room temperature, most preferably from 10° C. to 20° C. The resulting solution is cooled to −10° C. to −30° C., and triethylamine is added in 1.0 to 2.0 equivalents such that the temperature range is below 0° C. and the mixture aged for 1 hour. The mixture is filtered, and the filtrate cooled to 0° C.

For Amides:

The amine is added in 1.0 to 7.0 equivalents either neat or as a solution in THF and the reaction is aged for about 1–3 hours at room temperature. The reaction is quenched with 10% aqueous hydrochloric acid, washed with 10% sodium hydroxide followed by sodium chloride solution, and the solvent removed.

The crude product is purified by distillation or recrystallization depending on the physical properties. The reaction occurs in 40–80% mole yield based on 2,4,8-undecatrienoic acid.

For Esters:

Alcohol (10 eq) is added and the reaction is stirred overnight at room temperature. The reaction is quenched with 10% % aqueous hydrochloric acid, washed 5% sodium hydroxide solution and finally with water and the solvent is removed.

The crude product is purified by distillation and the reaction occurs in 60–85% mole yield based on 2,4,8-undecatrienoic acid.

The amides and esters are synthesized according to the general scheme above with the following specific examples. Equivalents set out are mole equivalents based on starting acid, yields are purified chemical yields based on starting acid.

The following examples I(A)–I(D) set forth syntheses of specific 2,4,8-undecatrienoic acid derivatives of our invention and include NMR data.

EXAMPLE I(A)

E2,E4,Z8-undecatrienoic acid

E2,E4,Z8-undecatrienal 1 eq, silver (I) oxide 1.1 eq, concentrated sodium hydroxide solution 1 weight eq, acidified to pH1 with conc. hydrogen chloride solution, yield=43%.

| | |
|---|---|
| 0.96 ppm | (t, 3H, J=7.53Hz) |
| 2.04 ppm | (quintet, 2H, J=7.41Hz) |
| 2.19 ppm | (t, 2H, J=6.27Hz) |
| 2.24 ppm | (t, 2H, J=6.23Hz) |
| 5.32 ppm | (m, 1H) |
| 5.40 ppm | (m, 1H) |
| 5.79 ppm | (d, 1H, J=15.35Hz) |
| 6.20 ppm | (m, 2H) |
| 7.34 ppm | (d, 1H, J=15.34Hz, of d, J=10.12Hz) |

EXAMPLE I(B)

N-isobutyl E2,E4,Z8-undecatrienamide

E2,E4,Z8-undecatrienoic acid 1 eq, ethyl chloroformate 1.5 eq, triethylamine 1.5 eq, isobutylamine 1.2 eq, quench as per general procedure, yield=75%.

| | |
|---|---|
| 0.93 ppm | (d, 6H, J=6.64 Hz) |
| 0.95 ppm | (t, 3H, J=7.52 Hz) |
| 1.80 ppm | (septet, 1H, J=6.73 Hz) |
| 2.03 ppm | (quintet, 2H, J=7.40 Hz) |
| 2.19 ppm | (m, 4H) |
| 3.17 ppm | (t, 2H, J=6.48 Hz) |
| 5.16–5.37 ppm | (m, 2H) |
| 5.39 ppm | (br. s, 1H) |
| 5.76 ppm | (d, 1H, J=15.01 Hz) |
| 6.02–6.19 ppm | (m, 2H, j) |
| 7.19 ppm | (d, 1H, J=14.96 Hz, of d, J=10.24 Hz) |

EXAMPLE I(C)

N,N-dimethyl E2,E4,Z8-undecatrienamide

E2,E4,Z8-undecatrienoic acid 1 eq, ethyl chloroformate 1.5 eq, triethylamine 1.5 eq, dimethylamine (2.0M solution in THF) 3.0 eq, quench as per general procedure, yield=67%.

| | |
|---|---|
| 0.95 ppm | (t, 3H, J=7.54Hz) |
| 1.25 ppm | (t, 3H, J=7.10Hz) |
| 2.03 ppm | (quintet, 2H, J=7.39Hz) |
| 2.19 ppm | (m, 4H) |
| 2.90 ppm | (s) |
| 3.01 ppm | (s, 3H) |
| 3.07 ppm | (s, 3H) |
| 4.11 ppm | (q, 2H, J=7.12Hz) |
| 5.28–5.43 ppm | (m, 2H) |
| 6.02–6.10 ppm | (m, 1H) |
| 6.17–6.25 ppm | (m, 1H) |
| 6.26 ppm | (d, 1H, J=14.79Hz) |
| 7.23 ppm | (d, 1H, J=14.76Hz, of d, J=10.26Hz) |

EXAMPLE I(D)

Methyl E2,E4, Z8-undecatrienoate

E2,E4,Z8-undecatrienoic acid 1 eq, ethyl chloroformate 1.5 eq, triethylamine 1.5 eq, methanol 10.0 eq, quench as per general procedure, yield=83%.

| | |
|---|---|
| 0.95 ppm | (t, 3H, J=7.53Hz) |
| 1.25 ppm | (t, 3H, J=7.15Hz) |
| 2.04 ppm | (quintet, 2H, J=7.67Hz) |
| 2.22 ppm | (m, 4H) |
| 3.73 ppm | (s, 3H) |
| 4.12 ppm | (q, 2H, J=7.14Hz) |
| 5.26–5.46 ppm | (m, 2H) |
| 5.80 ppm | (d, 1H, J=15.45Hz) |
| 6.08–6.23 ppm | (m, 2H) |
| 7.26 ppm | (d, 1H, J=15.39Hz, of d, J=9.97Hz) |

EXAMPLE 2

Preparation of an Alcoholic Beverage

The following formulation was prepared:

| Ingredients | Volume |
| --- | --- |
| 190° Proof food grade Ethyl Alcohol | 157.89 mL |
| High Fructose Corn Syrup 55 (77° Brix) | 217.00 mL |
| Citric Acid (50% solution) | 3.00 mL |
| Water | 622.11 mL |

Flavored beverages were prepared using the above 30° proof alcoholic base. A kiwi flavor was applied to the beverages. This flavor consisted of cis-3 hexenol, trans-2 hexenal, ethyl butyrate, ethyl-2-methyl butyrate, isoamyl butyrate, ethyl acetate, ethyl isovalerate, and trans-2-hexenol in equal proportions. The control beverage contained 200 ppm of the above flavor blend. This control beverage exhibited the taste characteristics of a candied kiwi flavor with moderate apple character. Another beverage was prepared containing 200 ppm of the same flavor and 3 ppm of N-isobutyl E2,E4,Z8-undecatrienamide prepared according to Example I(B). The flavor of this beverage was slightly more melon rind in character than the control. There was also an enhanced perception of alcohol and a tingle effect on the tongue.

EXAMPLE 3

Preparation of Hard Candy

The following formulation was prepared:

| Ingredients | Parts by Weight |
| --- | --- |
| Sucrose | 137 grams |
| Corn Syrup 42 DE | 91 grams |
| Water | 46 grams |

The above formulation was added to a stainless steel pot. With constant mixing, the formulation temperature was raised to 295° F. The pot was then removed from the heat, and 1.0 grams of a cola flavor containing the ingredients in equal amounts: cinnamic aldehyde, ginger oil, lemon oil, lime oil and nutmeg oil was added and blended with the sucrose-corn syrup-water formulation. After the blending was complete, 1.2 grams of citric acid was added. The resulting liquid candy was then deposited into molds, and the molds containing the liquid candy were cooled to room temperature, yielding 200 grams of finished hard candy. The resulting 'control candy' exhibited a typical cola flavor having citrus and spice taste and aroma nuances. A second candy sample was prepared using the above recipe modified by the addition of 50 ppm of N-isobutyl E2, E4, Z8-undecatrienamide prepared according the procedure of Example I (B). This second candy sample exhibited a moderately strong and substantive cola profile, as well as a taste effect similar to carbonation.

What is claimed is:

1. An E2,E4,Z8-undecatrienoic acid derivative defined according to the structure:

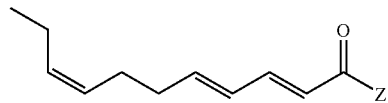

wherein Z represents —OR" or —NRR' with the provisos that when Z is —OR", R" is hydrogen, $C_1$–$C_6$ straight chain or branched-chain alkyl or $C_3$–$C_6$ straight chain or branched-chain alkenyl; and when Z is —NRR', R represents, in the alternative, hydrogen, methyl or ethyl and R' represents methyl, ethyl, n-propyl, cyclopropyl, isopropyl, n-butyl, sec-butyl, 2-methylbutyl, cyclobutyl,

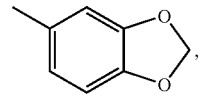

cyclopentyl or allyl.

2. The E2,E4,Z8-undecatrienoic acid derivative of claim 1 wherein Z is —NRR', R is selected from the group consisting of hydrogen, methyl and ethyl and R' is selected from the group consisting of hydrogen and $C_1$–$C_6$ alkyl.

3. The E2,E4,Z8-undecatrienoic acid derivative of claim 2 wherein Z is —NRR', R is methyl and R' is methyl.

4. The E2,E4,Z8-undecatrienoic acid derivative of claim 1 wherein Z is —OR" and R" is selected from the group consisting of hydrogen and methyl.

* * * * *